United States Patent [19]

Rentsch

[11] Patent Number: 6,136,312
[45] Date of Patent: Oct. 24, 2000

[54] METHOD FOR PRODUCING AN IGM PREPARATION FOR INTRAVENOUS APPLICATION

[75] Inventor: Markus Rentsch, Burgdorf, Switzerland

[73] Assignee: Rotkreuzstifung Zentrallaboratorium Blutspendedienst SRK, Burgdorf, Switzerland

[21] Appl. No.: 09/269,746

[22] PCT Filed: Oct. 14, 1997

[86] PCT No.: PCT/CH97/00388

§ 371 Date: Apr. 7, 1999

§ 102(e) Date: Apr. 7, 1999

[87] PCT Pub. No.: WO98/16558

PCT Pub. Date: Apr. 23, 1998

[30] Foreign Application Priority Data

Oct. 14, 1996 [EP] European Pat. Off. ............. 96810690

[51] Int. Cl.[7] .......................... C12N 9/50; A61K 39/395; C07K 16/00
[52] U.S. Cl. ..................... 424/177.1; 530/390.5; 530/387.1; 435/264
[58] Field of Search .................. 435/2, 269; 424/130.1, 424/177.1; 530/387.1, 389.1, 412, 390.5

[56] References Cited

U.S. PATENT DOCUMENTS 4,075,193  2/1978  Campbell et al. .
5,075,425  12/1991 Kotitschke et al. ................. 530/387

FOREIGN PATENT DOCUMENTS 0013901  8/1980  European Pat. Off. .
0120835  10/1984 European Pat. Off. .
0221505  5/1987  European Pat. Off. .
0221505  10/1987 European Pat. Off. .
0352500  1/1990  European Pat. Off. .
0413188  2/1991  European Pat. Off. .

OTHER PUBLICATIONS

Schiff P. et al Australian Paediatric Journal, 4:121–126 1968.
Anonymous, Pierce Catalog, pp. T67–Y70, Pierce Chemical Company, USA 1994.
P. Schiff et al, Australian Pediatric Journal, vol. 4, "The preparation, testing, and properties . . .", pp. 121–126, 1968.
J. T. Sgouris, VOX Sanguinis, vol. 13, No. 1, The preparation of plasmin treated immune . . . , pp. 71–84, Jul. 1, 1967.
M. M. Mayer, Experimental Immunochemistry, $2^{nd}$ Edition, "Complement and Complement Fixation", pp. 133–240, 1961.
P. Spath et al, Scand. J. Immunol., vol. 18, "An Extended C1q–Binding Assay Using Lactoperoxidase–. . . ", pp. 319–328, 1983.
W. k. Bleeker et al, VOX Sanguinis, vol. 52, "An Animal Model for the Detection of Hypotensive . . . ", pp. 281–290, 1987.

*Primary Examiner*—David Saunders
*Assistant Examiner*—Amy DeCloux
*Attorney, Agent, or Firm*—Jacobson, Price, Holman & Stern, PLLC

[57] ABSTRACT

In the method for producing an immunoglobulin solution suitable for intravenous application with an IgM proportion of more than 5% by weight with respect to the immunoglobulin proportion, an IgM-containing immunoglobulin solution is treated with a protease. The intravenously well tolerated preparation obtained is characterized by not being chemically modified and by having low anticomplementary activity ACA.

17 Claims, No Drawings

METHOD FOR PRODUCING AN IGM PREPARATION FOR INTRAVENOUS APPLICATION

This application claims priority to PCT/CH97/00388, filed Oct. 14, 1997.

This invention relates to a method of producing an immunoglobulin solution suitable for intravenous application. Used as the starting material is a protein fraction obtained from human or animal blood which contains the immunoglobulins in concentrated form.

As is well known, immunoglobulins play an important role in the immune system of man and mammal in fighting off infections. The immunoglobulins are divided up into different classes (e.g. IgG, IgA, IgM, IgD and IgE) with differing biochemical and physiological properties. Until 1980 only IgG was isolated and used as an IV-well-tolerated product for prophylaxis and therapy. In EP-A-0 013 901, EP-A-0 413 187 and EP-A-0 352 500 IgM preparations are described, which have been made intravenously well tolerated mainly through treatment with β-propiolactone. EP-A-0 413 188 describes a method in which the IV-tolerance is achieved through anion exchange chromatography with selective elution of the IV-tolerant fraction.

Object of the present invention is the production of a highly purified, IgM concentrate suitable for intravenous administration for therapy and prophylaxis. The product should have a low anticomplementary activity (ACA), and demonstrate a low blood pressure drop in a rat model, but the IgM molecules should not be chemically modified, however. This object was obtained surprisingly through treatment of a IgM-containing immunoglobulin solution with a protease.

The subject matter of the invention is therefore the method defined in claim 1.

The protease treatment is preferably an incubation at raised temperature in the presence of pepsin, papain, plasmin or thermolysine. The proteases can also be chemically modified, immobilized on a substrate and/or produced through genetic engineering. The preparation according to the inventive method can be transferred into an IV-administrable solution. Such a solution displays a reduction of the ACA, of the blood pressure drop in a rat model and of the C1q binding activity.

Suitable as starting materials for the method according to the present invention are immunoglobulin-containing solutions, such as, e.g. plasma, precipitate A or B from Kistler-Nitschmann-fractionation; Cohn fraction I/II/III; II/III; III; or other IgM-containing plasma fractions from human or animal plasma. For example, an immunoglobulin-containing fraction, such as precipitate B according to Kistler-Nitschmann, can be dissolved in a buffer, most of the impurities being removed through a precipitation with 0.5 to 5% octanoic acid at pH 4 to 6, preferably pH 5. Afterwards the solution is incubated at low ionic strength for 1 to 48 hours, preferably 9 hours, at a temperature of 20 to 50° C., preferably 37° C. with addition of at least 50 U/g of pepsin, preferably 600 U/G.

For further purification, the solution can be subjected to an adsorption, for example with a gel containing a DEAE-group in batch or column method. If the IgM concentration in the end product is supposed to be increased further, the IgM solution is put on an ion exchanger (e.g. TMAE-Fraktogel®). Through a selective elution, e.g. by means of a salt gradient or pH gradient, the IgM fraction can be isolated. Through ultrafiltration and diafiltration, for example a gel filtration, the solution can be concentrated and the electrolyte content can be adjusted to a final, intravenously well tolerated formulation. The protein concentration can amount to 1 to 20%, preferably 3 to 6%. The product can contain in addition proteins, preferably albumin, as well as sugar, preferably glucose or sucrose, or amino acids.

To assess the intravenous compatibility of immunoglobulin preparations, the anticomplementary activity (ACA) is usually used. To determine the ACA, a defined quantity of the product to be tested is incubated with a defined quantity of guinea pig complement and the remaining quantity of complement titrated. The ACA is indicated as consumption of CH50 per g of immunoglobulin. The indicated results of the ACA were determined to a large extent according to the method published by M. Mayer (Mayer, M. M. (1961), "Complement and Complement Fixation" in *Experimental Immunochemistry*, $2^{nd}$ edition, pp. 133–240, C Thomas, Springfield, Ill.). Valid as a guide value for intravenously usable IgG products is an ACA of <1000 CH50 per g of protein.

To assess intravenous compatibility, the binding of the C1q complement components to the immunoglobulin can be further used. For determination, a defined quantity of test product is incubated with a defined quantity of purified, radioactively labelled C1q complement in buffer and in serum. The C1q binding activity of the test product is determined through precipitation in the presence of polyethylene glycol. The higher the radioactivity in the precipitate, the greater the C1q binding activity of the product. Finer predictions about the type of C1q binding and thereby the quality of the product can be achieved if the C1q is radioactively labelled with two different methods. On the one hand, under as mild as possible oxidative conditions with lactoperoxidase (LPO), and, on the other hand, under drastic oxidative conditions with chloramine T (CT). The tests were carried out to a large extent according to the method published by P. Späth (P. J. Späth, A. Corvetta, U. E. Nydegger, R. Büttler: "An Extended C1q-Binding Assay Using Lactoperoxidase- and Chloramin-T-iodinated C1q," *Scand. J. Immunol.* 18, 319–328, 1983). Expected of an intact, intravenously well tolerated preparation is that the C1q binding activity is as minimal as possible. A model for testing the IV compatibility of immunoglobulins is the rat model according to Bleeker et al. [W. K. Bleeker, J. Agterberg, G. Rigter, A. de Vries-van Rossen, J. C. Bakker: "An Animal Model for the Detection of Hypotensive Side Effects of Immunoglobulin Preparations,", *Vox. Sang.* 52:281–290 (1987)]. Tolerance parameter in this model is blood pressure. Intravenously poorly tolerated products lead to a significant drop in blood pressure.

EXAMPLES

Reference Example 1

1 kg of precipitate B according to Kistler-Nitschmann was suspended in 4 kg of 0.1 mol/l acetate buffer, pH 5.1, and 2% octanoic acid was added at room temperature. 0.15 g of tricalcium phosphate was added per g of octanoic acid, and the precipitate filtered off. The filtrate was diafiltered against 20 mmol/l piperazine, 60 mmol/l NaCl, pH 5.8. The diafiltered solution was treated with 75 mg DEAE-Sephadex® per g of protein. Then the protein concentration was adjusted to 20 mg/ml, and the solution was treated with 1% Tweene® 80 and 0.3% TNBP (tri-n-butyl-phosphate) for 8 hours at 25° C. The solution was then put on a TMAE-Fraktogel® column, and the IgM fraction was eluted with 20 mmol/l piperazine, 160 mmol/l NaCl, pH 5.8. The end product was concentrated to 5% protein, and the pH value adjusted to 4.5.

Reference Example 2

1 kg of precipitate B according to Kistler-Nitschmann was suspended in 4 kg of 0.1 mol/l acetate buffer, pH 5.1, and 2% octanoic acid was added at room temperature. 0.15 g of tricalcium phosphate was added per g of octanoic acid, and the precipitate filtered off. The filtrate was diafiltered against 20 mmol/l NaCl diafiltered, and the solution brought to 20 mg/ml protein. The pH value was adjusted with 0.2 mol/l HCl to 4.0, and the solution incubated for 9 hours at 37° C. After cooling down to 20° C., the pH was adjusted to 5.8, and piperazine ad 20 mmol/l and NaCl ad 60 mmol/l added. The solution was subsequently treated with 1% Tween® 80 and 0.3% TNBP (tri-n-butyl-phosphate) for 8 hours at 25° C. The solution was then put on a TMAE-Fraktogel® column, and the IgM fraction was eluted with 20 mmol/l piperazine, 160 mmol/l NaCl, pH 5.8. The end product was concentrated to 5% protein, and the pH value adjusted to 4.5.

Example 1

1 kg of precipitate B according to Kistler-Nitschmann was suspended in 4 kg of 0.1 mmol/l acetate buffer, pH 5.1, and 2% octanoic acid was added at room temperature. 0.15 g of tricalcium phosphate was added per g of octanoic acid, and the precipitate filtered off. The filtrate was diafiltered against 20 mmol/l NaCl diafiltered, and the solution brought to 20 mg/ml protein. The pH value was adjusted with 0.2 mmol/l HCl to 4.0, and 600 U pepsin per g of protein were added. Then the solution was incubated for 9 hours at 37° C. After cooling down to 20° C., the pH was adjusted to 5.8, and piperazine ad 20 mmol/l and NaCl ad 60 mmol/l added. The solution was subsequently treated with 1 % Tween® 80 and 0.3% TNBP (tri-n-butyl-phosphate) for 8 hours at 25° C. The solution was then put on a TMAE-Fraktogel® column, and the IgM fraction was eluted with 20 mmol/l piperazine, 160 mmol/l NaCl, pH 5.8. The end product was concentrated to 5% protein, and the pH value adjusted to 4.5.

Example 2

1 kg of precipitate B was prepared analogously to reference example 2, instead of 600 U of pepsin per g of protein of the solution, 1200 U of pepsin per g of protein being added, however, before the pH 4 incubation.

I. Characterization of the Experimental Products

The immunoglobulins IgG, IgA and IgM were nephelometrically determined with antisera. The total protein content was determined with the Kjeldahl method.

|  | Protein mg/g | IgG mg/g | IgA mg/g | IgM mg/g | Isoagglutinins Anti-A | Anti-B |
|---|---|---|---|---|---|---|
| Reference example 1 | 44.4 | 4.1 | 16.8 | 45.0 | 1:64 | 1:64 |
| Reference example 2 | 48.1 | 8.6 | 19.3 | 43.5 | 1:128 | 1:64 |
| Example 1 | 51.3 | 7.0 | 22.0 | 50.5 | 1:128 | 1:64 |
| Example 2 | 46.9 | 4.7 | 20.2 | 51.0 | 1:128 | 1:64 |

TABLE II

Tolerance Parameters

|  | Treatment | ACA CH50/g | Rat model Blood pressure drop % | C1q-binding Puffer LPO % | C1q-binding Puffer CT % | C1q-binding Serum LPO % | C1q-binding Serum CT % |
|---|---|---|---|---|---|---|---|
| Reference example 1 | Without pH 4 | 515 | 19 | 1.5 | 0.1 | 43 | 5.5 |
| Reference example 2 | pH 4 | 179 | 18 | 0 | 0.5 | 42 | 6.7 |
| Example 1 | pH 4 with 600 U pepsin | 125 | 7 | 0 | 0.3 | 34 | 3.9 |
| Example 2 | pH 4 with 1200 U pepsin | 89 | 2 | 0 | 0.5 | 23 | 3.7 |

The addition of pepsin causes a reduction of the ACA, a lessening of the blood pressure drop in the rat model as well as a reduction in C1q binding activity.

I claim:

1. Method of producing an intravenously administrable polyclonal, immunoglobulin preparation, which is chemically not modified, with an IgM proportion of more than 5% by weight, with respect to the total immunoglobulin proportion, and an anticomplementary activity of <500 CH50/g protein, comprising the steps of:

selecting an IgM-containing plasma fraction;

preparing an aqueous solution or suspension from the IgM-containing plasma fraction, the IgM proportion in the aqueous solution or suspension being more than 5% by weight;

incubating the aqueous solution or suspension with a protease to reduce the anticomplementary activity of the aqueous solution or suspension to <500 CH50/g protein.

2. Method according to claim 1, characterized in that the preparation has an anticomplementary activity of <200 CH50/g protein.

3. Method according to claim 1, characterized in that the incubating step includes incubation of the aqueous solution or suspension at an acidic pH value and a temperature of at least 15° C.

4. Method according to claim 3, characterized in that the incubation temperature is 20 to 50° C.

5. Method according to claim 3, characterized in that the incubation period is 1 to 48 hours.

6. Method according to claim 1, characterized in that the incubating step includes a protease concentration in the aqueous solution or suspension of at least 50 U/g protein.

7. Method according to claim 1, characterized in that the pH value of the aqueous solution or suspension during the incubating step is 3.5 to 5.5.

8. Method according to claim 1, characterized in that the protease is an endopeptidase.

9. Method according to claim 8, characterized in that the protease is at least one endopeptidase selected from the group consisting of pepsin, papain, plasmin and thermolysine.

10. Method according to claim 1, characterized in that the ionic strength in the aqueous solution or suspension is <0.1.

11. The method according to claim 2, wherein the preparation has an anticomplementary activity of <150 CH50/g protein.

12. The method according to claim 4, wherein the incubation temperature is 35 to 40° C.

13. The method according to claim 5, wherein the incubation period is 6 to 12 hours.

14. The method according to claim 6, wherein the incubating step includes a protease concentration in the aqueous solution or suspension of 300 to 1200 U/g.

15. The method according to claim 7, wherein the pH value of the aqueous solution or suspension during the incubating step is 3.7 to 4.3.

16. The method according to claim 9, wherein the endopeptidase is immobilized on a substrate.

17. The method according to claim 10, wherein the ionic strength in the aqueous solution or suspension is <0.04.

* * * * *